United States Patent
Liu et al.

(10) Patent No.: US 9,101,316 B2
(45) Date of Patent: Aug. 11, 2015

(54) PORTABLE RADIATION DETECTOR AND SYSTEM

(75) Inventors: James Zhengshe Liu, Glenview, IL (US); Kenneth Scott Kump, Waukesha, WI (US); Gireesha C. Rao, Pewaukee, WI (US); Francisco Ruiz Gomez, Novi, MI (US); Xianfeng Ni, Sussex, WI (US); Rowland Frederick Saunders, Hartland, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 843 days.

(21) Appl. No.: 13/308,317

(22) Filed: Nov. 30, 2011

(65) Prior Publication Data
US 2013/0136235 A1 May 30, 2013

(51) Int. Cl.
*H05G 1/64* (2006.01)
*A61B 6/00* (2006.01)

(52) U.S. Cl.
CPC ............. *A61B 6/4233* (2013.01); *A61B 6/4283* (2013.01); *A61B 6/4405* (2013.01); *A61B 6/4494* (2013.01); *A61B 6/56* (2013.01)

(58) Field of Classification Search
CPC .. A61B 6/4233; A61B 6/4283; A61B 6/4405; A61B 6/4494; A61B 6/56
USPC ..................................... 378/19, 98, 98.8, 189
See application file for complete search history.

(56) References Cited

U.S. PATENT DOCUMENTS

| | | | |
|---|---|---|---|
| 7,649,979 B2 | 1/2010 | Liu et al. | |
| 7,724,875 B2 | 5/2010 | Jabri et al. | |
| 7,852,985 B2 | 12/2010 | Liu et al. | |
| 7,873,145 B2 | 1/2011 | Liu et al. | |
| 7,963,697 B2 | 6/2011 | Lamberty et al. | |
| 8,217,568 B2 | 7/2012 | Liu et al. | |
| 8,243,883 B2 | 8/2012 | Omernick et al. | |
| 8,396,188 B2 | 3/2013 | Liu et al. | |
| 2006/0272421 A1* | 12/2006 | Frinak et al. ................... 73/710 |
| 2010/0111263 A1* | 5/2010 | Lamberty et al. ............ 378/189 |
| 2010/0123083 A1 | 5/2010 | Petrick et al. | |
| 2011/0013220 A1 | 1/2011 | Avinash et al. | |
| 2012/0128116 A1 | 5/2012 | Sabol et al. | |
| 2012/0128125 A1 | 5/2012 | Jabri et al. | |
| 2012/0177183 A1 | 7/2012 | Liu et al. | |
| 2012/0189098 A1 | 7/2012 | Liu et al. | |
| 2012/0189100 A1 | 7/2012 | Liu et al. | |
| 2012/0275678 A1 | 11/2012 | Liu et al. | |
| 2013/0034213 A1 | 2/2013 | Liu et al. | |
| 2013/0034215 A1 | 2/2013 | Liu et al. | |

OTHER PUBLICATIONS

U.S. Appl. No. 13/588,760, filed Aug. 17, 2012, Liu et al.
U.S. Appl. No. 13/588,832, filed Aug. 17, 2012, Liu et al.
U.S. Appl. No. 13/568,912, filed Aug. 17, 2012, Liu et al.
(Continued)

*Primary Examiner* — Irakli Kiknadze
(74) *Attorney, Agent, or Firm* — Fletcher Yoder P.C.

(57) ABSTRACT

A portable detector for use with an imaging system is disclosed. The portable detector automatically sets one or more operational states based on at least a determination as to whether the portable detector is connected to external power. An imaging system is also disclosed that ascertains whether the portable detector is connected via a tether. The imaging system may perform a compatibility check when connected to the portable detector to assess compatibility between the imaging system and the portable detector.

20 Claims, 8 Drawing Sheets

(56) References Cited

OTHER PUBLICATIONS

U.S. Appl. No. 13/588,708, filed Aug. 17, 2012, Liu et al.

U.S. Appl. No. 13/569,890, filed Aug. 8, 2012, Liu et al.

U.S. Appl. No. 13/648,062, filed Oct. 9, 2012, Konkle et al.

* cited by examiner

PORTABLE RADIATION DETECTOR AND SYSTEM

BACKGROUND

A number of non-invasive imaging approaches are known and are presently in use. One such type of system is based upon the detection of X-rays that have passed through a volume of interest. The X-rays traverse the volume, and whatever materials occupy the volume, and impact a film or a digital detector. In medical diagnostic contexts, for example, such systems may be used to visualize internal tissues and diagnose patient ailments. In other contexts, parts, baggage, parcels, and other materials may be imaged to assess their contents or for other purposes, such as for quality review in a manufacturing context.

Increasingly, such X-ray systems use digital circuitry, such as solid-state detectors, for detecting the X-rays. Such solid-state detectors may generate electrical signals indicative of the incident X-rays on the detector, which in turn are indicative of the attenuation or scatter of X-rays along different ray paths through the imaged volume. The generated signals may in turn be processed to reconstruct images of the subject of interest within the volume, including internal features of an object or patient within the imaged volume.

In practice, an X-ray imaging system may have a fixed detector or be associated with a particular type of detector. Such arrangements may be useful for imaging purposes as an appropriate detector is used with a given imaging system. However, such an arrangement may be relatively inflexible with respect to changing detector capabilities.

BRIEF DESCRIPTION

In accordance with one embodiment, a portable detector configured to be used with different imaging systems is disclosed. The portable detector comprises one or more connectors through which external power can be provided to the portable detector and at least one memory structure encoding one or more routines. The one or more routines, when executed, specify an operational state of the portable detector based on input received from the one or more connectors. The portable detector also comprises one or more processors configured to execute the one or more routines encoded by at least one memory structure.

In accordance with another embodiment, an imaging system is provided. The imaging system includes a radiation source configured to emit radiation through an imaging volume and a tether connector configured to connect to a tether. The tether is configured to connect to a complementary connector of a portable detector that is separable and removable from the imaging system. The imaging system also comprises a controller configured to execute one or more routines which, when executed, determine whether the portable detector is connected to the imaging system via the tether.

In accordance with a further embodiment, an imaging system is provided. The imaging system comprises a radiation source configured to emit radiation through an imaging volume and an interface for communicating with a portable detector. The imaging system further comprises a controller configured to execute one or more routines which, when executed, determine the compatibility between the imaging system and the portable detector.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As discussed herein, portable digital X-ray detectors may be used with, and exchanged between, various radiological imaging systems. For example, a portable digital X-ray detector may be used with various types of X-ray imaging systems, such as imaging systems that are specific to an imaging or examination room or mobile systems that may be transported to different sites for imaging purposes. Likewise, a portable digital X-ray detector may be used as an interchangeable digital cassette providing an upgrade to an older system, such as replacing an analog film cassette. In different implementations, portable digital X-ray detectors may be capable of being powered by battery or by external power, depending on the context. Likewise, data exchange with such a portable digital X-ray detector may be via a wireless or wired connection, depending on the imaging context. In implementations discussed herein, one or more routines executing on a portable detector may be used to set an operational state of a portable detector based on the presence or absence of external power and/or of a wired or wireless data connection. In addition, one or more routines executing on an imaging system utilizing a portable detector may provide an indication as to whether the portable detector is connected to the imaging system by a tether or other wired connection. Further, upon connection of a portable detector to an imaging system, compatibility checks may be performed to confirm compatibility between the portable detector and the imaging system, with software updates applied to the portable detector as needed.

With the foregoing in mind, one or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosed subject matter, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
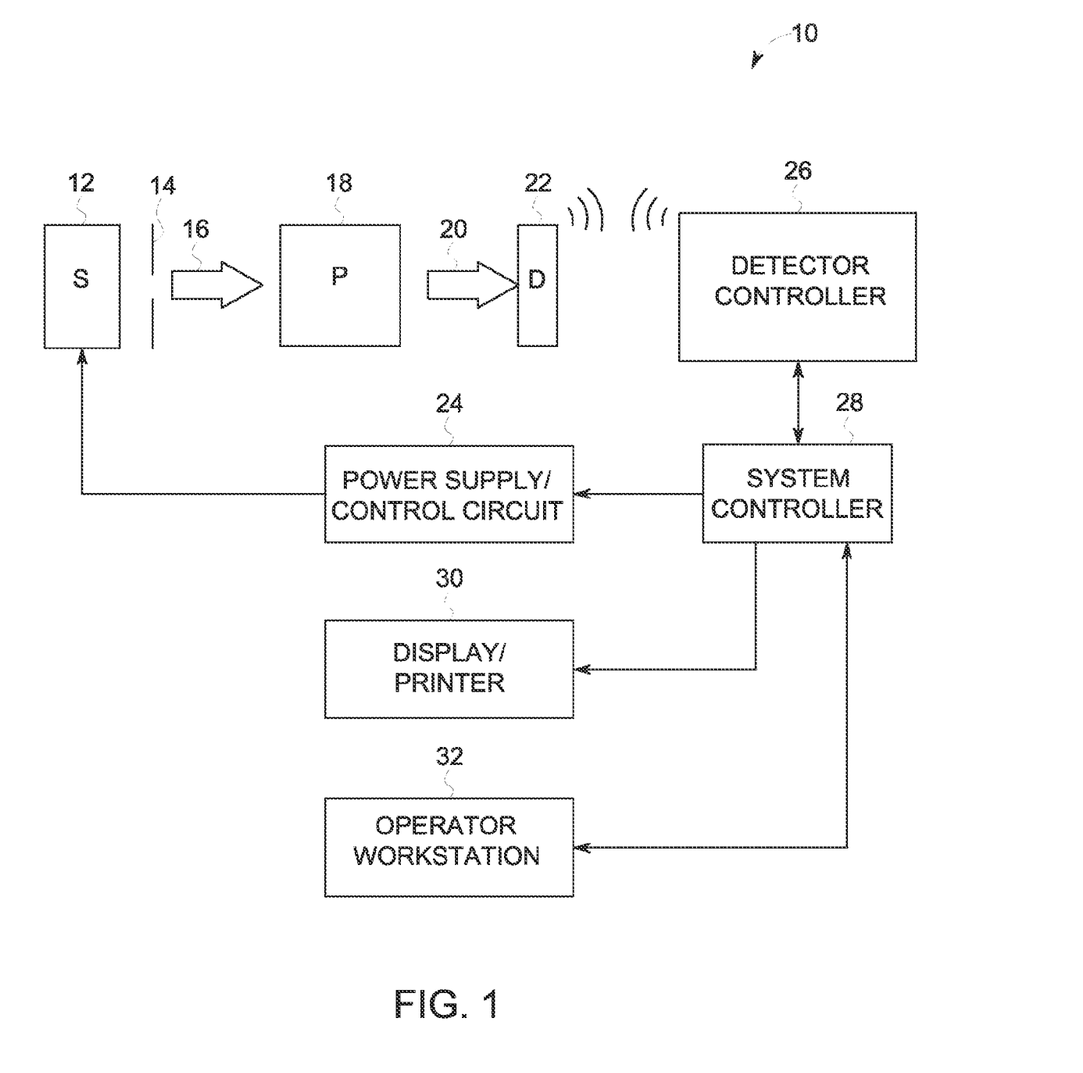
FIG. 1 is a diagrammatical overview of a digital X-ray imaging system in accordance with one or more embodiments of the present disclosure.

With the foregoing comments in mind and turning to FIG. 1, this figure illustrates diagrammatically an example of an imaging system 10 for acquiring and processing discrete pixel image data using a portable detector as discussed herein. In the illustrated embodiment, the imaging system 10 is a digital X-ray system designed both to acquire original image data and to process the image data for display. In the embodiment illustrated in FIG. 1, imaging system 10 includes a source of X-ray radiation 12 positioned adjacent to a collimator 14. The collimator 14 shapes and/or limits a stream of radiation 16 that passes into a region in which an object or subject, such as a patient 18, is positioned. A portion of the radiation 20 passes through or around the subject and impacts a portable digital X-ray detector, represented generally at reference numeral 22. As will be appreciated by those skilled in the art, the portable detector 22 may convert the X-ray photons incident on its surface to lower energy photons, and subsequently to electric signals, which are acquired and processed to reconstruct an image of the features within the subject.

The radiation source 12 is controlled by a power supply/control circuit 24 which supplies both power and control signals for examination sequences. Moreover, the portable detector 22 is communicatively coupled to a detector controller 26 which commands acquisition of the signals generated in the portable detector 22. In the depicted example, the portable detector 22 communicates wirelessly with the detector controller 26 via a suitable wireless communication standard. In other embodiments, the portable detector 22 can communicate with the detector controller 26 over a wire or cable, such as via a tether arrangement. The detector controller 26 may execute various signal processing and filtration functions, such as for initial adjustment of dynamic ranges, interleaving of digital image data, and so forth.

Both the power supply/control circuit 24 and the detector controller 26 are responsive to signals from a system controller 28. In general, the system controller 28 commands operation of the imaging system 10 to execute examination protocols and to process acquired image data. In the present context, the system controller 28 also includes signal processing circuitry, typically based upon a programmed general purpose or application-specific digital computer; and associated manufactures, such as optical memory devices, magnetic memory devices, or solid-state memory devices, for storing programs and routines executed by a processor of the computer to carry out various functionalities, as well as for storing configuration parameters and image data; interface protocols; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, the system controller 28 is linked to at least one output device, such as a display or printer as indicated at reference numeral 30. The output device may include standard or special purpose computer monitors and associated processing circuitry. One or more operator workstations 32 may be included in or otherwise linked to the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
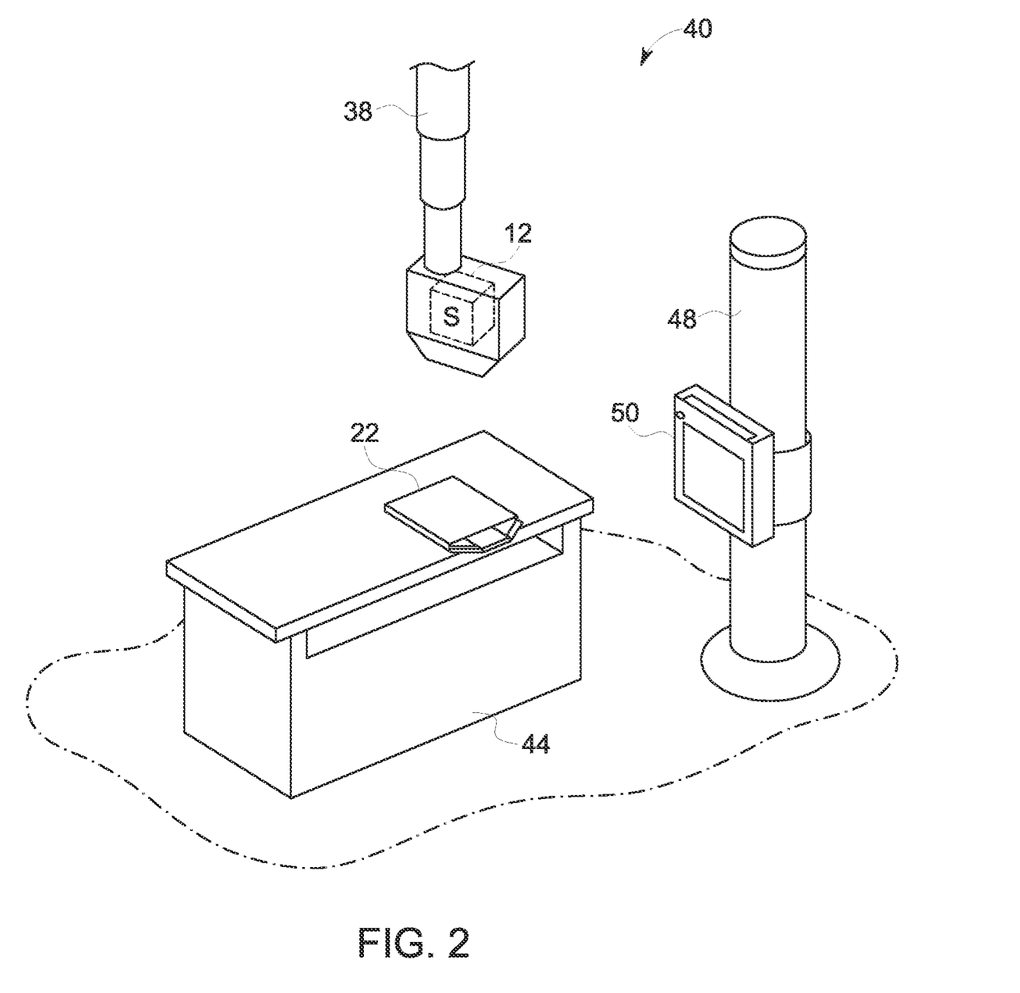
FIG. 2 is a perspective view of a fixed implementation of the digital X-ray imaging system of FIG. 1 in accordance with one embodiment.

By way of further example, a perspective view of a fixed or stationary imaging system 40 is provided in FIG. 2 in the context of a dedicated examination or imaging room. In this example, the imaging system 40 is incorporated into the room, i.e., fixed in place, and a patient is brought into the room for the purpose of imaging. The depicted imaging system 40 includes an overhead tube support arm 38 for positioning the radiation source 12, such as an X-ray tube, with respect to the patient 18 and the detector 22. It is also noted that, in addition to the radiation source 12, the imaging system 40 may also include any or all of the other components described above with respect to FIG. 1, such as the system controller 28.

Moreover, in one embodiment, the fixed imaging system 40 may be used with one or both of a patient table 44 or a wall stand 48 to facilitate image acquisition. Particularly, the table 44 and the wall stand 48 may be configured to receive or support one or more separable and portable detectors 22. For instance, the portable detector 22 may be placed on the upper surface of the table 44, and the patient 18 (or an anatomy of interest of the patient 18) may be positioned on the table 44 between the portable detector 22 and the radiation source 12. Alternatively, the portable detector 22 may be positioned vertically with respect to the table 44 for cross-table image acquisitions. Further, the wall stand 48 may include a receiving structure 50 also adapted to receive the portable detector 22, and the patient 18 may be positioned adjacent the wall stand 48 to enable image data to be acquired via the portable detector 22. Similarly, in other embodiments, the portable detector 22 may be placed in any suitable location for receiving the detector. For example, the portable detector 22 may also be placed in or on a device on which the patient is moved, such as behind the patient when the patient is located in a wheelchair or underneath the patient when the patient is on a gurney or mobile bed. Likewise, the portable detector 22 may be placed on the floor to perform standing exams, and so forth.

Figure 3:
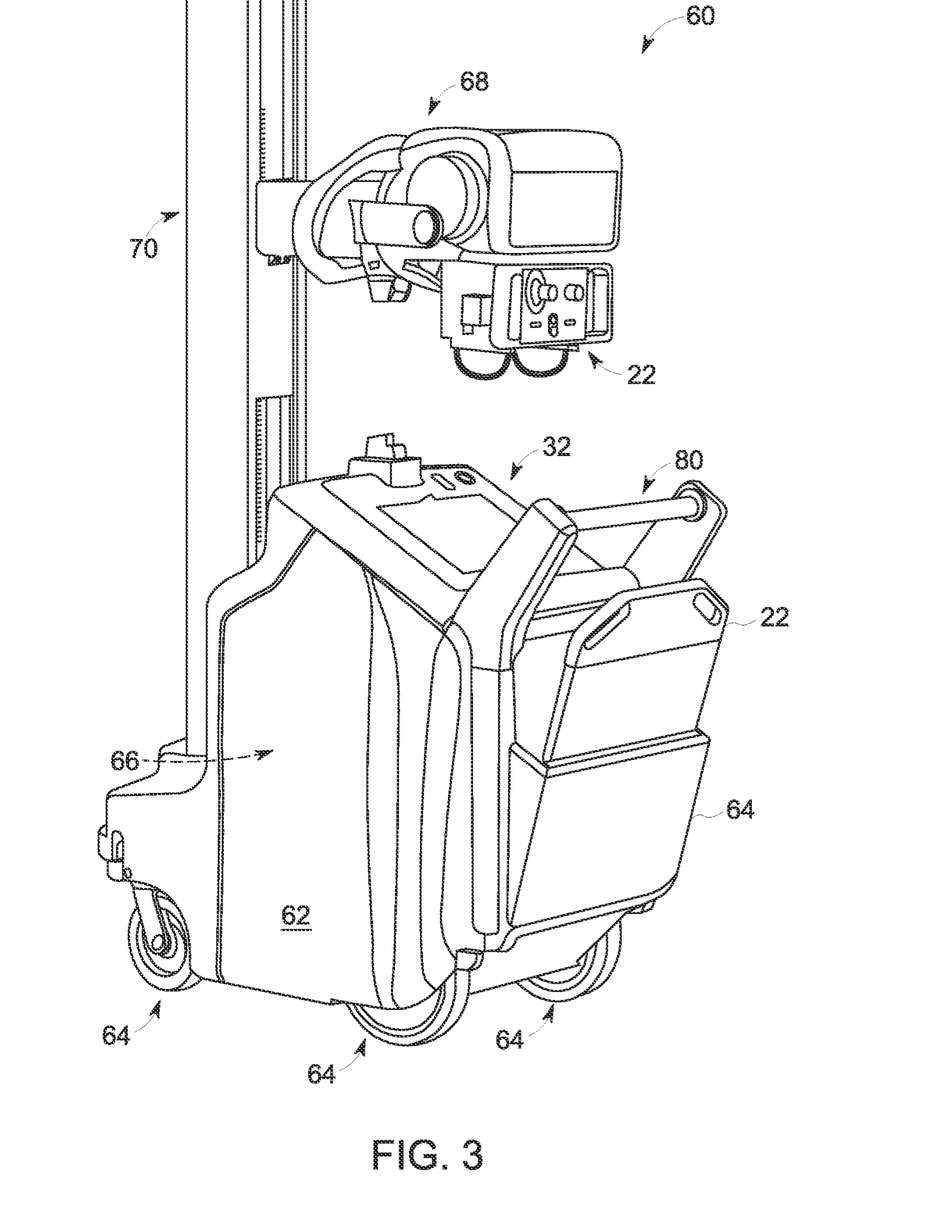
FIG. 3 is a perspective view of a mobile implementation of the digital X-ray imaging system of FIG. 1 in accordance with one embodiment.

In one embodiment, the imaging system 40 may be a stationary system disposed in a fixed X-ray imaging room, such as that generally depicted in, and described above with respect to FIG. 2. In other embodiments, however, the portable detector 22 may be utilized in a mobile X-ray imaging system 60, as depicted in FIG. 3. In one embodiment, the mobile imaging system 60 may be a digital X-ray system designed to acquire original images or image data and to process the image data for display.

The mobile X-ray imaging system 60 may be moved to a patient location, such as a patient recovery room, an emergency room, a surgical suite or operating room, and so forth, without requiring transport of the patient to a dedicated (i.e., fixed) X-ray imaging room. To facilitate movement of the mobile X-ray imaging system 60, the mobile system 60 may include a portable cart 62, which enables a user to move the imaging system 60 from one location to another. Attached to the portable cart 62 is a detector bin 64, which may be configured to receive one or more portable detectors 22. The detector bin 64 may be used to store and/or charge the portable detector 22 when the portable detector 22 is not being used.

The portable cart 62 shown in FIG. 3 may also include a support arm 68 that may be vertically moved along a support column 70 to facilitate positioning of a radiation source 12. Further, one or both of the support arm 68 and support column 70 may also be configured to allow rotation of the radiation source 12 about an axis. Further, the portable cart 62 includes wheels 64, which enable the user to move the mobile imaging system 60. In one implementation, the portable cart 62 houses system electronic circuitry 66 (e.g., detector controller 26 and/or system controller 28) that acquires image data from the portable detector 22 and that, where properly equipped, may process the data to form desired images. In other embodiments, such as where the portable detector 22 represents an upgrade in technology or capability, the image data may not be communicated from the portable detector 22 to the mobile imaging system 60 but to a remote system which will process the data and/or generate images. The system electronic circuitry 66 both provides and controls power to the radiation source 12 and the portable cart 62 using a power source, such as a battery or transformer. The portable cart 62 may also include an operator workstation 32 and display that enables the user to interact with and operate the mobile imaging system 60. The workstation 32 may include buttons, switches, or the like to facilitate operation of the mobile imaging system 60. Finally, the portable cart 62 may include a handle 80 to facilitate movement of the mobile imaging system 60 by the user.

Figure 4:
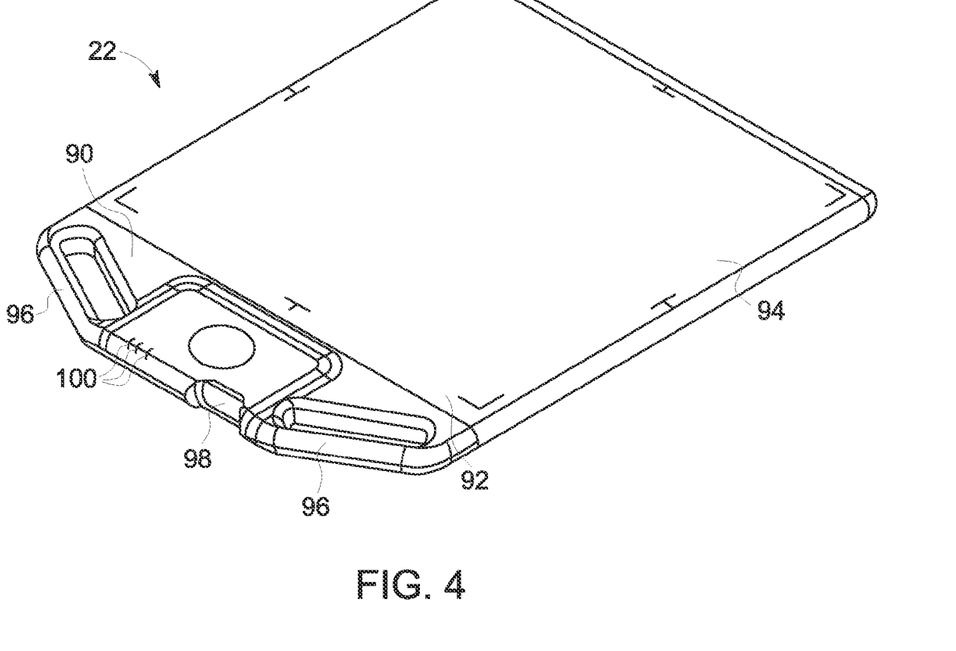
FIG. 4 is a perspective view of a portable digital detector, in accordance with aspects of the present disclosure.
Figure 5:
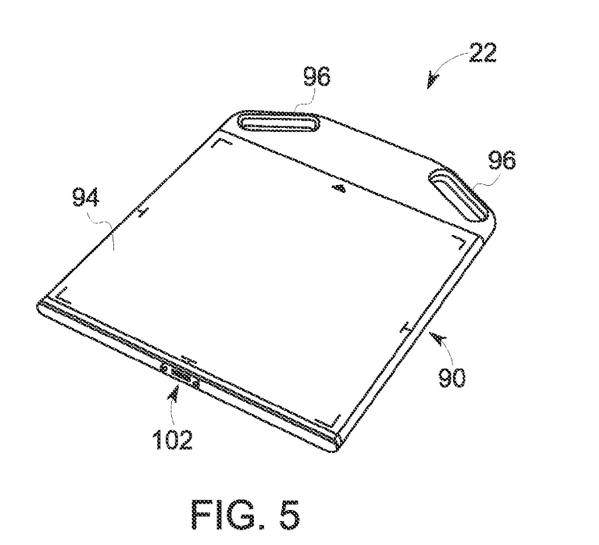
FIG. 5 is an alternative perspective view of the portable digital detector of FIG. 4, in accordance with aspects of the present disclosure.
Figure 6:
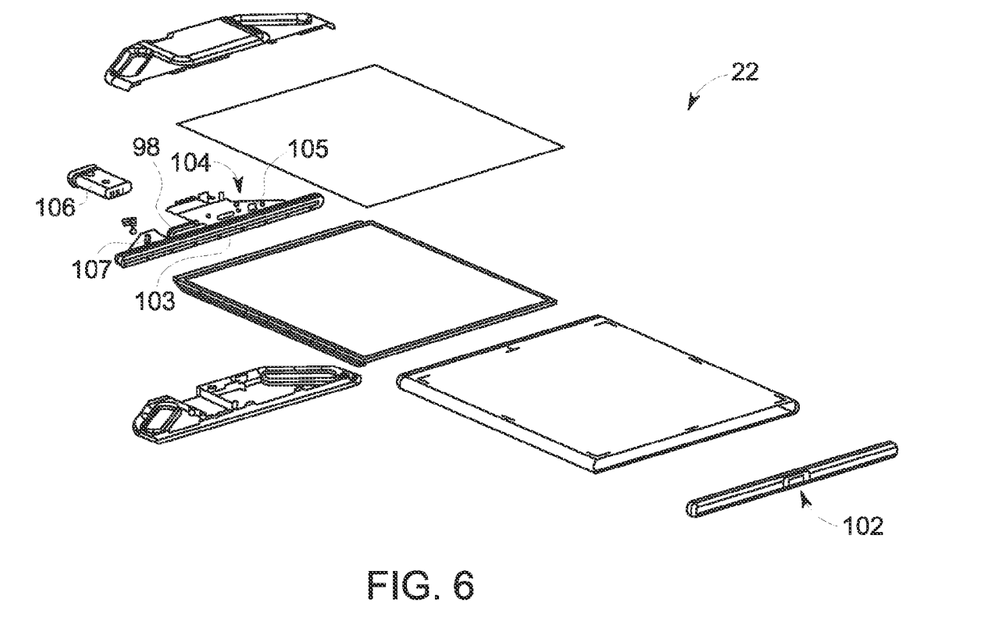
FIG. 6 is an exploded perspective view of the portable digital X-ray detector, as shown in FIG. 4, in accordance with one embodiment.

With the foregoing discussion of imaging systems in mind, it should be appreciated that such systems may be used in conjunction a portable detector 22, as discussed herein. An example of one embodiment of a portable detector 22 is generally illustrated in FIGS. 4-6, with FIG. 6 providing an exploded view of certain components of interest. In the illustrated embodiment, the portable detector 22 may include a housing 90 that encloses various components of the detector 22. In certain embodiments, the housing 90 includes a window 92 that exposes a surface of the solid-state detector array 94 on which radiation is directed during use. As discussed above, when in use, the detector array 94 may be configured to receive electromagnetic radiation, such as from the radiation source 12, and to convert the radiation into electrical signals that may be interpreted by the imaging system 10 to output an image of an object or patient 18. The housing 90 may include one or more handles 96 that facilitate positioning and transport of the detector 22 by a technician or other user.

In one embodiment, operating power may be provided to the portable detector 22 via a connector 98 (e.g., receptacle) configured to engage either a removable battery 106 (FIG. 6) or a cable (e.g., a tether). The portable detector 22 may communicate with one or more other components of the imaging system 10, such as the detector controller 26 and/or system controller 28, via a wireless transceiver disposed within the body of the portable detector 22.

Alternatively, the portable detector 22 may also communicate data over a wired connection, such as via a tether coupled to the portable detector 22 by way of the connector 98, or via another cable or structure coupled to a docking connector 102 (FIG. 5) provided elsewhere on the portable detector 22. For example, in one embodiment, the docking connector 102 may be positioned on the portable detector 22 so as to engage a complementary structure when inserted into a table 44 or receiving structure 50 of a wall stand 48 in the context of a fixed imaging system 40. In this manner, the docking connector 102 may be used to provide power to the detector 22 and to allow data communication (such as gigabit Ethernet communication) between the detector 22 and other components of an imaging system. Likewise, the docking connector 102 may be configured to mate with a complementary structure within a storage bin for the detector 22 such that the detector 22 may be charged during storage.

In one embodiment, the portable detector 22 may include one or more memory structures 103 or one or more processor 105, among the electronic components 104 (FIG. 6). Among other things, the memory structures may store image or X-ray attenuation data acquired via the detector array 62 and/or may store executable routines for reading data acquired by the detector panel or for automatically determining and setting a state of the portable detector 22, as discussed herein. That is, in some implementations, a memory structure of the detector 22 may store firmware or other executable code or parameters that determine or facilitate operation of the detector 22. The portable detector may also include one or more sensors 107, such as an accelerometer, a proximity sensor, a motion sensor, a light sensor, and so forth, that generate responsive signals in response to an environmental cue, such as motion, acceleration, light intensity, and so forth. Additionally, in some embodiments, the housing 90 may include various indicators 100, such as light-emitting diodes, that communicate detector power, status, operation, or the like to a user.

To the extent that portable detectors 22 may be employed that are not affixed or assigned to a particular X-ray imaging system 10, it may be useful for such portable detectors 22 to be interchangeable with respect to different imaging systems. For example, in a clinical setting where numerous imaging systems of various types (including imaging systems of fixed and mobile design, as discussed above) are present, it may be useful for a portable detector 22 to be used with a variety of the X-ray imaging systems present. However, depending on the imaging context, the operation of portable detector 22 may vary. For example, in certain contexts, the portable detector 22 may be employed with a tether or other wired attachment that provides power and allows data transfer over the tether. Conversely, in other contexts, the portable detector 22 may operate off battery power and may communicate wirelessly.

Figure 7:
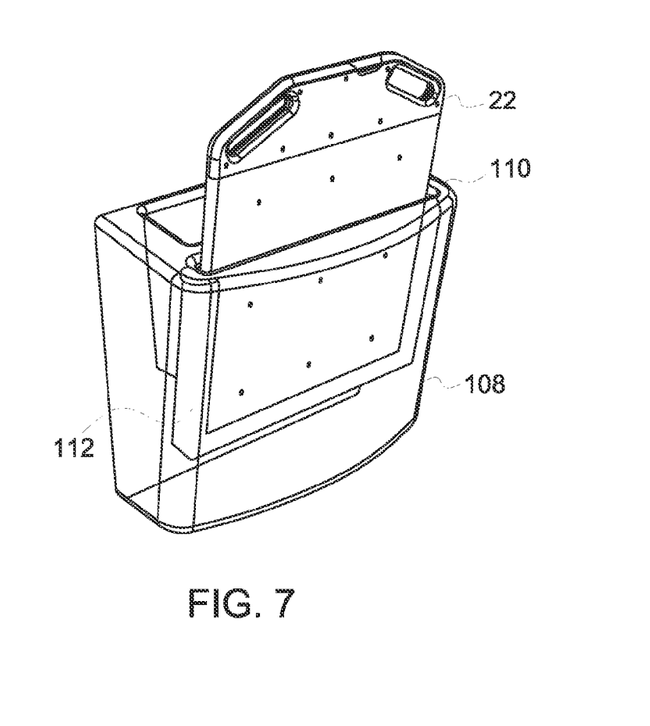
FIG. 7 is perspective view of a detector inserted into a detector bin in accordance with aspects of the present disclosure.

As noted above, in certain implementations, the portable detector 22 may be stored when not in use and, in particular, the portable detector 22 may be stored in a dedicated bin or receptacle specifically configured to receive the portable detector 22. For example, FIG. 7 depicts a perspective view of one such detector bin 108. As illustrated in FIG. 7, the detector 22 is inserted into the detector bin 108. In the illustrated embodiment, the detector bin 108 includes a detector slot 110 configured to receive the detector 22. In certain embodiments, the detector bin 108 may include more than one detector slot 110 to enable the detector bin 108 to receive more than one detector 22. A guide rail 112 may be present inside the detector bin 108 and may guide the detector docking connector 102 toward a complementary detector bin connector when the detector 22 that charges the detector 22 when it is inserted in the detector bin 108.

With this in mind, in certain embodiments the operation or storage, an operational state of the portable detector 22 may be automatically determined based on whether the portable detector 22 is in storage or based upon the type of imaging system 10 with which the digital detector is being used. For example, an operational state of the portable detector 22 may be determined based upon whether the portable detector 22 is currently powered by battery power or external power and/or by whether the portable detector 22 is relying on wireless or wired data communication, or is not currently exchanging data at all. Therefore, in certain implementations discussed herein, the various power and/or data configurations may be determined automatically by the portable detector 22 so as to place the portable detector 22 in a suitable power and/or data transmission state based on whether or how the detector 22 is currently being used.

By way of example, in one implementation a portable detector 22 may have various defined power states, such as an IDLE state in which power consuming components are powered down. In such a state, data modules and/or circuitry of the portable detector 22 (i.e., the readout circuitry) may be powered off and supporting electrical components such as fans which typically cool internal electronics of the portable detector 22 may also be off, though the detector panel itself may be powered on. The portable detector 22 may enter such an IDLE state when not connected to wired power (i.e., when powered by a battery) and when not in use for an imaging application.

The portable detector 22 may be configured to enter a STANDBY state when connected to external power but when not currently in use for an imaging application. In such a STANDBY state, the portable detector 22 may charge any battery that is present and may continue to perform routine detector operations, such as charging and reading the detector elements between imaging operations. Likewise, power consuming components such as fans may be on. In the STANDBY state, the portable detector 22 is essentially at full power, but is not currently used in an imaging operation.

Similarly, in an IMAGING state, the portable detector 22 is fully powered, including the detector elements and fans. However, unlike the STANDBY state, signals read out from the detector elements are saved or transmitted to detector controller instead of being discarded. That is, in the IMAGING state, the portable detector 22 is actually in use in either a mobile imaging system 60 or fixed imaging system 40.

Lastly, the portable detector 22 may be placed in a CHARGING state, such as when in a detector bin or otherwise connected to external power outside of an imaging context. In such a charging state, the portable detector 22, or a battery within the detector 22, may be charged, but the detector elements and associated electronic components (e.g., fans) may be powered off.

By way of illustration, the following examples describe real-world, clinical situations that may prompt automatic state determination and changes in a portable detector 22 as discussed herein. For example, in one embodiment, a portable detector 22 may be placed in a detector bin 108 that includes a connector that mates with and charges the portable detector 22. In such an embodiment, the routines executing on the portable detector 22 may automatically determine that the CHARGING state is appropriate and place the detector 22 in such as state.

Upon being removed from the detector bin 108, the portable detector 108, in one implementation, may enter a digital cassette mode in which the portable detector 22 is powered by an internal battery and communicates data wirelessly. Such a digital cassette mode may be suitable for use with a mobile imaging system 60 or other imaging system where there is not external power or wired data transmission, such as where the portable detector 22 is being used as an upgrade to an existing system. In such a context, once the portable detector 22 is removed from the detector bin 108, routines executing on the portable detector 22 may place the portable detector 22 in an IDLE state in which the panel of the portable detector 22 is powered up while the readout circuitry is not powered. In the IDLE state, the portable detector 22 is ready to acquire images in a digital cassette mode, but is not currently acquiring images.

In an example, of a digital cassette mode application, the routines executing on the portable detector 22 may switch the portable detector 22 from an IDLE state to an IMAGING state upon receipt of an indication that the portable detector 22 is in use in an imaging application, such as when an operator actuates an exposure controller (e.g., a hand switch) indicative of an image acquisition operation. Alternatively, in other implementations, a sensor 107 present in the portable detector 22 may generate a signal in response to motion, light, or some other factor that causes the portable detector 22 to go from an IDLE state to an IMAGING state (or a STANDBY state, discussed below). For example, a proximity sensor may generate a signal in response to a person moving to within a specified proximity to the portable sensor 22 or an accelerometer may generate a signal in response to the portable detector 22 being picked up. In these examples, the signal generated by the sensor 107 may be indicative of pending use of the portable detector 22, causing the portable detector 22 to go from the IDLE state to the IMAGING state or the STANDBY state.

In the IMAGING state, the portable detector 22 is fully powered, including the readout circuitry and ancillary electrical components (e.g., fans) that participate in data acquisition. Data readout by the readout circuitry in the IMAGING state is saved, stored, and/or communicated to the detector acquisition circuitry for further processing. Once the data acquisition operation is complete, the routines executing on the portable detector place the portable detector back in an IDLE state, in the absence of external power.

If, however, the portable detector 22 is not used in a digital cassette mode but is instead used in a fixed room application (i.e., in a table or wall stand application in which power and wired data communication are provided), the routines executing on the portable detector 22 may operate differently. For example, in one such implementation the portable detector 22 may be in an IDLE state prior to connection to a fixed room imaging system but, once connected, the routines executing on the portable detector may respond to the presence of external power and/or wired data communication by placing the portable detector 22 in a STANDBY state in which all electronics (including readout circuitry) are powered up and ready for imaging at any time. As noted above, a signal from a sensor 107 (e.g., a proximity sensor or accelerometer) may also be a factor that contributes to the portable detector 22 going from an IDLE state to a STANDBY state. Though the readout circuitry may be operation in the STANDBY state, data readout may be discarded or otherwise not stored as no imaging operation is currently being performed. Further, in the STANDBY state, a battery in the portable detector 22 may be charged.

Upon receiving an indication that an imaging operation is being performed, such as when an operator actuates an exposure controller (e.g., a hand switch) indicative of an image acquisition operation, the routines executing on the portable detector 22 may switch the portable detector 22 from a STANDBY state to an IMAGING state. In the IMAGING state, the portable detector 22 is fully powered, including the readout circuitry and ancillary electrical components (e.g., fans) that participate in data acquisition and data readout by the readout circuitry is saved, stored, and/or communicated to the detector acquisition circuitry for further processing. Once the data acquisition operation is complete, the routines executing on the portable detector place the portable detector back in a STANDBY state.

Figure 8:
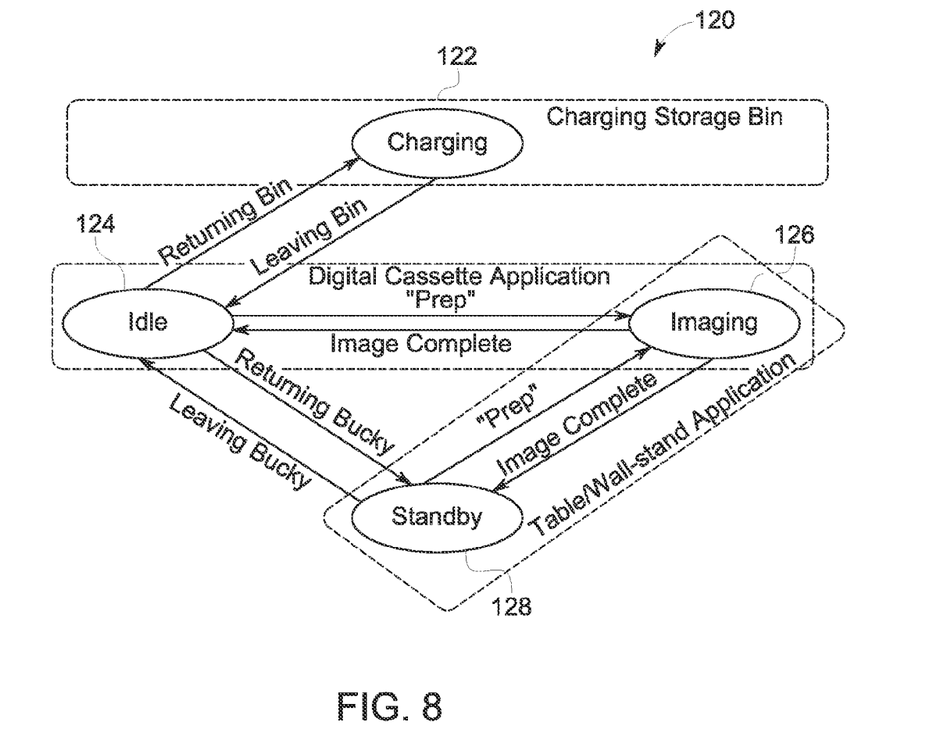
FIG. 8 graphically depicts a state flow diagram for a portable detector in accordance with aspects of the present disclosure.

A visual state diagram 120 depicting the various possible states discussed above in the context of the provided examples is provided in FIG. 8. As will be appreciated, the above examples and depicted state are not-exhaustive and are merely illustrative on one possible implementation provided as an example. As depicted in the state diagram, a portable detector 22 is placed in a CHARGING state 122 when in a suitably equipped detector bin 108. Upon being removed from the detector bin 108, the portable detector 22 runs on battery power is placed in an IDLE state 124. If the portable detector 22 is used in a digital cassette operation, and remains disconnected from external power, the portable detector 22 switches between the IDLE state 124 and an IMAGING state 126, depending on whether an imaging operation is being performed or not.

In the event that the portable detector is not used in a digital cassette application but is instead used in a fixed room or other imaging application in which external power is present, the portable detector 22 does not run on battery power but instead operates on the provided external power. In this example, the portable detector 22 is placed in a STANDBY state 128 once connected to the external power source. The portable detector 22 switches between the STANDBY state 128 and the IMAGING state 126, depending on whether an imaging operation is being performed or not. Once imaging is completed, the portable detector 22 may be disconnected from the external power source, resulting in the portable detector being placed in an IDLE state until it is either used another imaging operation or placed in a detector bin 108 for charging.

With the foregoing in mind, one example of inputs or status data that may be used in conjunction with executable routines to automatically set a state of a portable detector 22 is connection data determined from the connectors 98 or 102. For example, turning to FIG. 9, an example of a pin layout for a docking connector 102 is depicted. In accordance with this example, four pair of Ethernet pins 140 are provided toward the outside of the docking connector 102, two pair of power return pins 142 are provided, as are two pair of +12V pins 144, and a pair of pins 146 used to determine whether the portable detector is connected to a detector bin 108 or to a table 44 or wall stand 48 of a fixed imaging system 40.

Figure 9:
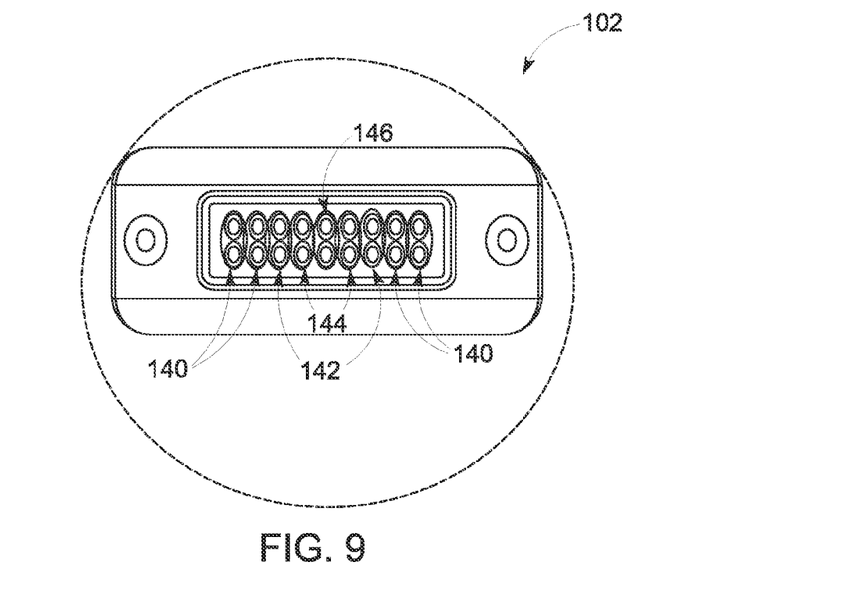
FIG. 9 depicts a pin layout for a docking connector of a portable detector in accordance with aspects of the present disclosure.

In one implementation using such a pin layout, the state may be determined by sensing the presence of power applied on the docking connector 108 as well as the resistance on the bin/dock sensing pins 146, such as where the bin/dock sensing pins 146 are open on the docking connector 102 when the portable detector 22 is in a detector bin 108 and are shorted when the portable detector 22 is connected to a table 22 or wall stand 48.

For example, using this pin information, an initial determination may be made as to whether the portable detector 22 is connected to external power or not, such as using the power return pins 142. If the portable detector 22 is determined to not be connected to external power, the portable detector 22 is placed in an IDLE state 124 (or an IMAGING state 126 if data acquisition has been commanded).

If the portable detector is determined to be connected to external power, an additional determination may be made as to whether portable detector 22 is located in a detector bin 108 for charging and storage or is connected to an imaging system for data acquisition. As noted above, in one implementation, the voltage is measured across the bin/dock sensing pins 146, with an open voltage indicate of the portable detector 22 being located in a detector bin 108 and a closed voltage indicative of the portable detector 22 being connected to an imaging system. If the portable detector 22 is determined to be located in a detector bin, the status of the portable detector 22 may be set to CHARGING 122. If the portable detector 22 is determined to be connected to an imaging system and in the presence of external power, the portable detector 22 is placed in a STANDBY state 128 (or an IMAGING state 126 if data acquisition has been commanded).

Figure 10:
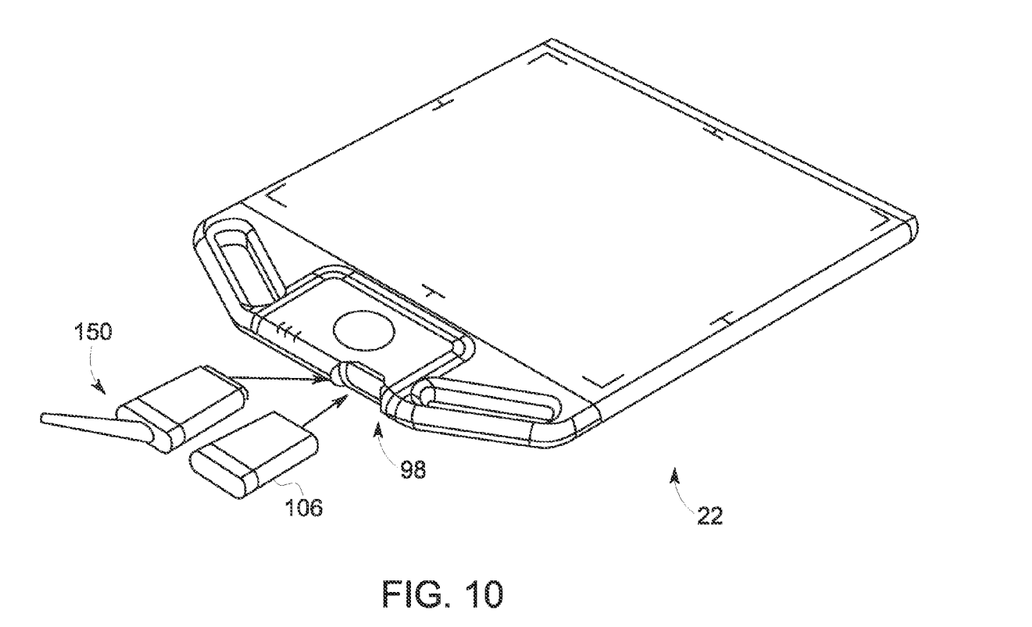
FIG. 10 depicts the alternative use of a battery or tether with a portable detector in accordance with aspects of the present disclosure.

In addition, in certain implementations the portable detector 22 may be operated using a tether 150 which attaches to the portable detector 22, such as via connector 98. In such implementations, routines executing on the portable detector 22 may automatically detect the presence of the tether 150 and operate the portable detector 22 accordingly. For example, in one implementation, the tether 150 may be used to provide power and communication when a docking connection or wireless communication are not available. In such an instance, a tether 150 may be connected to the portable detector 22 at connector 98 in place of battery 106. For example, in such an implementation, the portable detector 22 may automatically detect the presence of the tether 150 and may direct communications over the wired connection provided by the tether 150, such as over a wired Ethernet connection.

Figure 11:
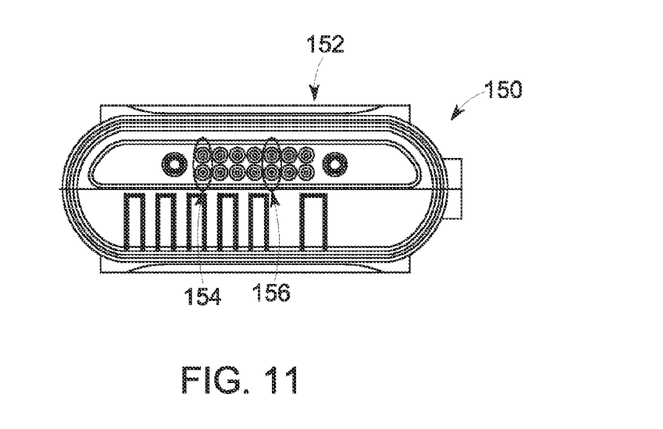
FIG. 11 depicts a pin layout for a plug of a tether in accordance with aspects of the present disclosure.

By way of example, FIG. 11 depicts a tether connector 152 having a pair of detector present pins 154 used by an imaging system to provide indication to the imaging system that a portable detector 22 is connected via the tether 150 and a pair of tether sense/sense return pins 156 that allow the portable detector 22 to determine the presence of the tether 150. For example, in one implementation where such a tether connector 152 pin layout is employed, the tether sense/sense return pins 156 are shorted at the connector 98 inside the portable detector 22. In such an implementation, an imaging system can determine the presence of a tethered connection to the portable detector 22 by sensing the resistance change over the tether sense/sense return pins 156. That is, the imaging system senses a short when the portable detector 22 is connected through the tether 150 and an open circuit when the portable detector is not connected by a tether 150. Based on this determination, the imaging system provides power via the tether 150 and/or directs communication through the tether 150. Likewise, routines executing on the portable detector 22 may make a similar determination as to the presence of a tether 150 via an open or shorted connection at the tether sense/sense return pins 156 and may set a state of the portable detector 22 (or may otherwise adjust operation of the portable detector 22) accordingly.

While the preceding describes various embodiments in which a status of a portable detector 22 is automatically set or by which an imaging system automatically recognizes a type of connection to a portable detector 22, in other embodiments it may be useful to automatically determine the compatibility between a portable detector 22 and imaging system. For example, different imaging systems and/or portable detectors may be on different maintenance, update, or replacement schedules and, thus, may be characterized by different hardware and software versions and revisions. Therefore, it may be useful to automatically assess the compatibility between an imaging system and portable detector prior to use.

Figure 12:
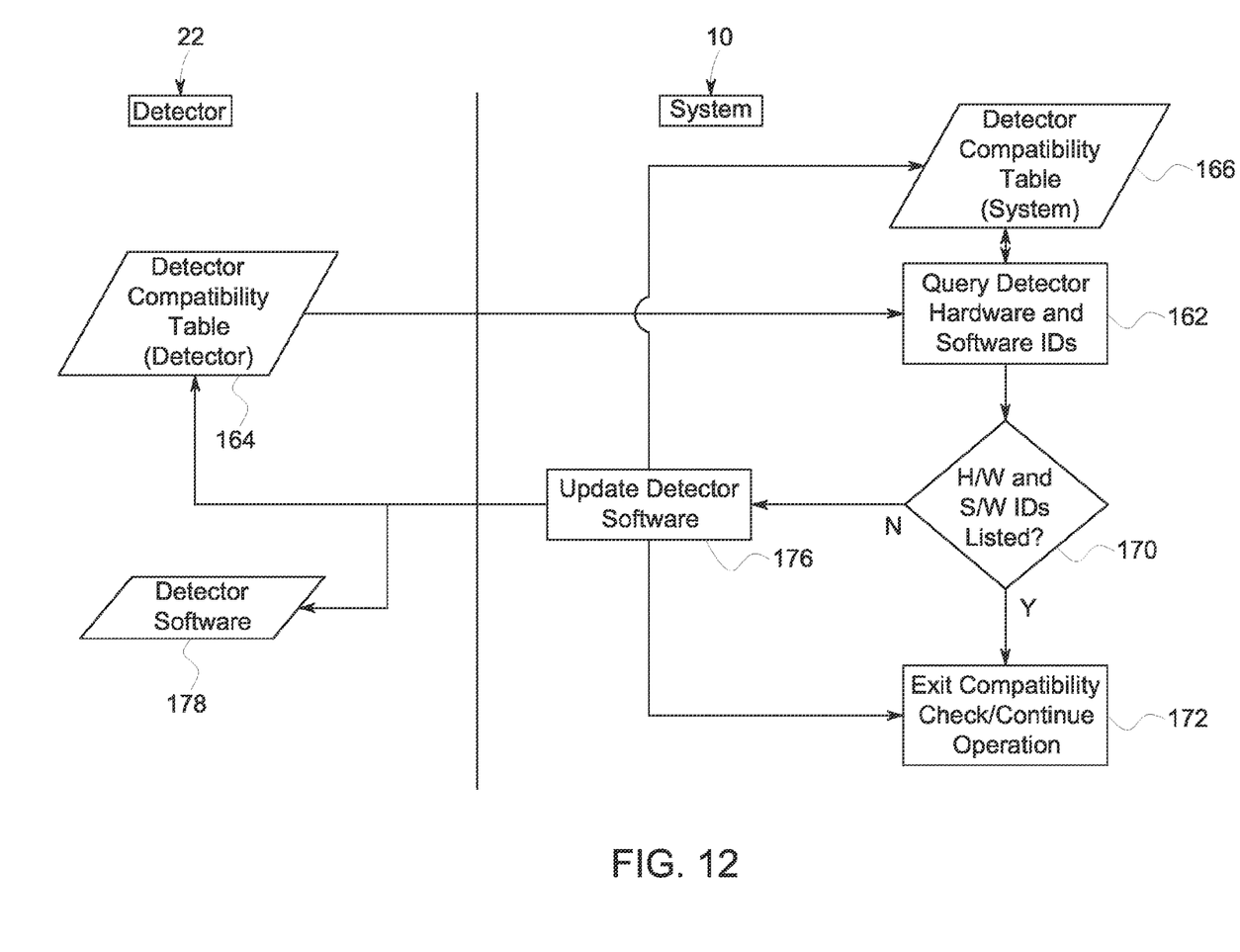
FIG. 12 depicts a flow diagram of a compatibility check process in accordance with aspects of the present disclosure.

For example, turning to the flowchart 160 of FIG. 12, when a portable detector 22 is connected to an imaging system 10, either by docking or via wireless connection, the imaging system 10 performs a compatibility check, such as to assess the firmware version of the portable detector 22. Typically the detector hardware will be compatible with all imaging systems 10. However, in the event that a hardware incompatibility is determined to exist, as discussed below, a warning message may be displayed indicating the incompatibility and/or any suggested corrective action to be taken.

With respect to software incompatibilities, the imaging system 10 may query (block 162) a detector compatibility table 164 stored on the portable detector 22 or a detector compatibility table 166 stored on the system itself, whichever is newer. For example, based on a revision or version number associated with each detector compatibility table, the query 162 may be directed to the most current detector compatibility table. In certain embodiments, the detector compatibility table determined to be the most current may be used to overwrite the other detector compatibility table such that both the portable detector 22 and the imaging system 10 store the most recent version of the detector compatibility table. That is, if the portable detector 22 has the more recent version of the detector compatibility table 164, the detector compatibility table 166 stored on the imaging system 10 may be overwritten with the detector compatibility table 164 retrieved from the portable detector 22. Conversely, if the imaging system 10 has the more recent version of the detector compatibility table 166, the detector compatibility table 164 stored on the portable detector 22 may be overwritten with the detector compatibility table 166 stored on the imaging system 10.

In practice, the detector compatibility table 164, 166 may contain unique identifiers for each system or system model or type as well as information on each of the portable detector hardware and software revisions as depicted in Table 1 and 2 below, where Table 1 illustrates an earlier or older revision (i.e., Rev 3) of a detector compatibility table and Table 2 illustrates a later version (i.e., Rev 4) in which additional system (i.e., System 6) and detector software (i.e., Det. SW5) information has been added:

TABLE 1

| Rev 3 | Det. HW1 | Det. HW2 | Det. HW3 | Det. SW1 | Det. SW2 | Det. SW3 | Det. SW4 |
|---|---|---|---|---|---|---|---|
| System 1 | Y | Y | Y | Y | Y | | |
| System 2 | Y | Y | Y | Y | Y | Y | |
| System 3 | Y | Y | Y | | Y | Y | |
| System 4 | Y | | Y | | Y | Y | Y |
| System 5 | | Y | Y | | | Y | Y |

TABLE 2

| Rev 4 | Det. HW1 | Det. HW2 | Det. HW3 | Det. SW1 | Det. SW2 | Det. SW3 | Det. SW4 | Det. SW5 |
|---|---|---|---|---|---|---|---|---|
| System 1 | Y | Y | Y | Y | Y | | | |
| System 2 | Y | Y | Y | Y | Y | Y | | |
| System 3 | Y | Y | Y | | Y | Y | | |
| System 4 | Y | | Y | | Y | Y | Y | |
| System 5 | | Y | Y | | | Y | Y | |
| System 6 | | Y | Y | | | | | Y |

During a compatibility check, the imaging system 10 queries (block 162) the most recent available table (e.g., table 164 or table 166) based on the system identifier and the detector hardware and software configurations to determine (block 170) compatibility. If both the detector hardware and software configurations are listed in the appropriate table as being compatible with the system 10 in question, the system 10 exits (block 172) the compatibility check and continues with the imaging operation.

If, the detector hardware configuration is not listed as being compatible with the system 10 in question, the system 10 may display a message alerting the operator that the portable detector 22 in question is not compatible with the imaging system 10. In this situation, the imaging system 10 may also provide contact or service information to assist the operator in obtaining resolution to the hardware incompatibility.

In the event that a software incompatibility is determined to exist (i.e., the detector software version is not compatible with the imaging system 10 in question) the imaging system 10 may download or otherwise access the latest compatible software for the portable detector 22. The compatible software version may then be applied as an update (block 176) to the detector software 178. Upon updating of the detector software, the imaging system 10 exits (block 172) and continues with the imaging operation. In certain implementations, one or both of the detector compatibility tables 164, 166 may be updated to reflect the software version of the portable detector 22 after application of a software update.

Technical effects include the automatic determination of an operational state of a portable detector. In particular, in one implementation, an operational state of a portable detector is automatically set based upon whether the portable detector is powered by battery or external power or whether the portable detector has a wired or wireless data connection. Other technical effects include the automatic detection of a tethered connection of a portable detector to an imaging system. An additional technical effect includes the automated compatibility assessment of a portable detector with an imaging system. In the event of a software incompatibility, the portable detector may be updated with more current software to achieve compatibility.

This written description uses examples to disclose the present subject matter, including the best mode, and also to enable any person skilled in the art to practice the disclosed subject matter, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable detector that transduces electromagnetic radiation into electrical signals and that is configured to be used with different imaging systems, the portable detector comprising:
   one or more connectors configured to provide external power to the portable detector;
   at least one memory structure encoding one or more routines which, when executed, specify an operational state of the portable detector based on input received from the one or more connectors;
   one or more processors configured to execute the one or more routines encoded by the at least one memory structure.

2. The portable detector of claim 1, wherein the one or more connectors comprise a docking connector configured to connect to a complementary connector of a storage location or imaging system and to receive power through the complementary connector when so connected.

3. The portable detector of claim 1, wherein at least one operational state specified by the portable detector being connected to external power causes one or more power-consuming components of the portable detector to be turned on.

4. The portable detector of claim 1, wherein at least one operational state specified by the portable detector being powered by a battery causes one or more power-consuming components of the portable detector to be turned off.

5. The portable detector of claim 1, wherein the operational state of the portable detector is determined at least in part based upon whether the one or more connectors are connected to an external power source.

6. The portable detector of claim 1, wherein the operational state of the portable detector is determined at least in part based upon whether the one or more connectors are connected to a storage container for holding and charging the portable detector or to an imaging system connector.

7. The portable detector of claim 1, wherein the operational state of the portable detector is determined at least in part in response to a signal generated by an accelerometer or a proximity sensor.

8. The portable detector of claim 1, wherein the input received from the one or more connectors comprises an indication as to whether an open voltage or a closed voltage exists with respect to one or more pair of pins of the one or more connectors.

9. An imaging system, comprising:
   a radiation source configured to emit radiation through an imaging volume;
   a tether connector configured to connect to a tether, wherein the tether is configured to connect to a complementary connector of a portable detector that is separable and removable from the imaging system; and
   a controller configured to execute one or more routines which, when executed, determine whether the portable detector is connected to the imaging system via the tether.

10. The imaging system of claim 9, wherein the controller is configured to receive an input from a plug of the tether and wherein the input is used to determine whether the tether is connected to the portable detector.

11. The imaging system of claim 10, wherein the input from the plug comprises an indication as to whether an open voltage or a closed voltage exists with respect to one or more pair of pins of the plug.

12. The imaging system of claim 9, wherein the controller is further configured to provide power via the tether when the tether is connected to the portable detector.

13. The imaging system of claim 9, wherein the controller is further configured to provide a data connection via the tether when the tether is connected to the portable detector.

14. An imaging system, comprising:
   a radiation source configured to emit radiation through an imaging volume;
   an interface for communicating with a portable detector; and
   a controller configured to execute one or more routines which, when executed, determine the compatibility between the imaging system and the portable detector.

15. The imaging system of claim 14, wherein the one or more routines, when executed, determine the compatibility between the imaging system and the portable detector by accessing at least one detector compatibility table stored on the portable detector or the imaging system.

16. The imaging system of claim 14, wherein the one or more routines, when executed:
   access a first detector compatibility table stored on the portable detector and a second detector compatibility table stored on the imaging system;
   determine whether the first detector compatibility table or the second detector compatibility table is more current; and
   determine the compatibility between the imaging system and the portable detector based on the contents of the more current detector compatibility table.

17. The imaging system of claim 16, wherein the one or more routines, when executed, overwrite a less current detector compatibility on the portable detector or imaging system with the more current detector compatibility table.

18. The imaging system of claim 14, wherein the one or more routines, when executed:
   download a software update for the portable detector when a software incompatibility is determined to exist; and
   update the portable detector with the software update.

19. The imaging system of claim 18, wherein the one or more routines, when executed, update at least one detector compatibility table based on the software update being applied to the portable detector.

20. The imaging system of claim 14, wherein the one or more routines, when executed, display a notification message when a hardware incompatibility is determined to exist.

* * * * *